US011691000B2

(12) United States Patent
Heo

(10) Patent No.: US 11,691,000 B2
(45) Date of Patent: Jul. 4, 2023

(54) BONE CONDUCTION APPARATUS HAVING TENS THERAPY FUNCTION

(71) Applicant: MOBIFREN CO., LTD, Gyeongsangbuk-do (KR)

(72) Inventor: Joo Won Heo, Dalseo-gu Daegu (KR)

(73) Assignee: MOBIFREN CO., LTD, Gumi-si (KR)

( * ) Notice: Subject to any disclaimer, the term of this patent is extended or adjusted under 35 U.S.C. 154(b) by 64 days.

(21) Appl. No.: 16/968,825

(22) PCT Filed: Aug. 19, 2019

(86) PCT No.: PCT/KR2019/010464
§ 371 (c)(1),
(2) Date: Aug. 10, 2020

(87) PCT Pub. No.: WO2020/040497
PCT Pub. Date: Feb. 27, 2020

(65) Prior Publication Data
US 2021/0162203 A1 Jun. 3, 2021

(30) Foreign Application Priority Data
Aug. 20, 2018 (KR) .......................... 10-2018-0096809

(51) Int. Cl.
*A61N 1/36* (2006.01)
*A61N 1/04* (2006.01)
*H04R 1/10* (2006.01)

(52) U.S. Cl.
CPC ......... *A61N 1/0456* (2013.01); *A61N 1/3603* (2017.08); *A61N 1/36036* (2017.08); *H04R 1/10* (2013.01); *H04R 2460/13* (2013.01)

(58) Field of Classification Search
CPC ................ A61N 1/0456; A61N 1/3603; A61N 1/36036; A61N 1/36034; A61N 1/36014; H04R 1/10; H04R 2460/13; H04R 25/606
See application file for complete search history.

(56) References Cited

U.S. PATENT DOCUMENTS 5,354,321 A 10/1994 Berger
2001/0031996 A1 10/2001 Leysieffer
(Continued)

FOREIGN PATENT DOCUMENTS

JP S62-101249 A 5/1987
JP H10-57441 A 3/1998
(Continued)

OTHER PUBLICATIONS

International Search Report issued in connection with PCT Application No. PCT/KR2019/010464 dated Dec. 12, 2019.

*Primary Examiner* — Amanda K Hulbert
*Assistant Examiner* — Natasha Patel
(74) *Attorney, Agent, or Firm* — Hauptman Ham, LLP

(57) ABSTRACT

A bone conduction apparatus according to the present invention includes: a decoding unit decoding audio data; a digital-to-analog converter converting the decoded audio data to an analog signal, and outputting an analog audio signal; a bone conduction unit converting the analog audio signal to a bone conduction signal, and outputting the bone conduction signal; a metal electrode placed at an outside of a housing in which the bone conduction unit is provided; a frequency generator generating a transcutaneous electrical nerve stimulation (TENS) signal; and a TENS signal amplification unit amplifying the TENS signal, and applying the resulting signal to the metal electrode.

4 Claims, 4 Drawing Sheets

(56) References Cited

U.S. PATENT DOCUMENTS

| | | |
|---|---|---|
| 2011/0046687 A1 | 2/2011 | Naschberger |
| 2012/0245406 A1 | 9/2012 | Aghamohammadi |
| 2014/0126752 A1* | 5/2014 | Beck .................. A61N 1/36036 |
| | | 381/151 |
| 2015/0119635 A1* | 4/2015 | Gustafsson .......... H04R 25/606 |
| | | 704/271 |
| 2015/0382115 A1* | 12/2015 | Meskens .............. H04R 25/606 |
| | | 381/326 |
| 2017/0135896 A1* | 5/2017 | Snow .................. A61H 23/0218 |
| 2017/0156010 A1* | 6/2017 | Verma ................ A61N 1/36038 |
| 2017/0353807 A1 | 12/2017 | Lim et al. |
| 2017/0368329 A1* | 12/2017 | Tyler ........................ A61N 1/32 |

FOREIGN PATENT DOCUMENTS

| | | |
|---|---|---|
| JP | 2001-137363 A | 5/2001 |
| JP | 3187620 U | 12/2013 |
| KR | 10-2008-0011985 A | 2/2008 |
| KR | 10-1648195 B1 | 8/2016 |
| KR | 10-1876666 B1 | 7/2018 |
| WO | 2014-081452 A1 | 5/2014 |
| WO | 2016/109851 A1 | 7/2016 |
| WO | 2018/106839 A2 | 6/2018 |

\* cited by examiner

BONE CONDUCTION APPARATUS HAVING TENS THERAPY FUNCTION

TECHNICAL FIELD

The present invention relates to a bone conduction apparatus. More particularly, the present invention relates to a bone conduction apparatus having a TENS therapy function.

BACKGROUND ART

In general, there are two ways a human can hear sound: an air conduction method and a bone conduction method.

The air conduction method is a method in which sound is transmitted to the inner ear through a tympanic membrane. In general, vibration of sound transmitted through the air is transmitted to the tympanic membrane in the ear, and the vibration is transmitted to the cochlea through three bones positioned in the tympanic membrane.

The bone conduction method is a method in which sound through the cranial bone is transmitted to the cochlea, and is transmitted through the auditory nerve to the brain. In the sound recognition mechanism, the process of the vibration passing through the tympanic membrane and the three bones positioned in the tympanic membrane is omitted.

That is, the sound vibration applied to the skin surface around the ear is directly transmitted to the cochlea through the cranial bone. Thus, even a person having hearing loss due to a problem in the tympanic membrane or auditory ossicles is able to hear sound using bone conduction through the skin, if the cochlea and the auditory nerve are normal.

Air-conduction-type earphones and headphones are used with the ears closed, so the user is unable to hear nearby ambient noise, resulting in an increase in the risk of accidents. Therefore, advanced countries legally prevent listening to music, and the like on the road wearing air-conduction-type earphones and headphones used with the ears closed.

In addition, due to the recent remarkable spread of digital sound and communication devices, adolescent noise-induced hearing loss has increased worldwide, and 10% or more of the population have hearing loss. In the global aging era, an increase in age-related hearing loss is a social issue. As a measure to prevent such hearing loss, it is suggested that the volume of the receiving speaker and the time of use should be reduced.

Therefore, an ordinary person uses the bone conduction speaker with the ears opened, so the nearby ambient noise is also received. Since the principle of bone conduction is used, accidents and hearing loss are prevented without direct influence on the tympanic membrane.

In the meantime, electroanalgesia is a type of therapy for pain that applies electricity to a human body internally or externally. In general, the electroanalgesia is intended to prevent transmission of a pain signal from a point of a pain source to the brain.

One well known type of electroanalgesia is transcutaneous electrical nerve stimulation (hereinafter, referred to as TENS) therapy. TENS provides comfort and delight to a person in a way that treats various types of pain, or in a way that is often considered somewhat similar to acupuncture.

In general, it is accepted that a human body responds well to various predetermined individual frequencies. Therefore, it is known that devices using TENS provide vibrating transcutaneous energy to electrodes positioned on several parts of the human body, thereby providing comfort and delight.

Regarding the use of TENS, there are many clinical reports regarding use thereof for various types of pain, such as lower back pain, muscle and fascia pain, arthritis, pain related to the sympathetic nerve, pain in the bladder, urinary incontinence, neurogenic pain, visceral pain, postsurgical pain, and the like.

TENS is the application of electrical stimulation to the surface of the skin and is mainly for the relief of pain. TENS treatment is performed through an external surface electrode using several types of electrical waveforms characterized by frequency, pulse width, and amplitude.

Relieving pain by applying electricity has been known for a long time, but gained practical attention after Melzack and Wall's announcement of the gate control theory in 1965. The gate control theory provides the scientific basis for a pain relief mechanism. TENS is non-pharmacological, non-invasive, and non-addictive, and has almost no contraindications.

A general TENS therapy uses a relatively high stimulation frequency (for example, 50 to 150 Hz) and a low current (for example, 1 to 2 mA), which are the values that most users can endure. Alternatively, a low stimulation frequency (for example, 1 to 5 Hz) and a high current (for example, 15 to 80 mA) may be used, which may be better than the general therapy for some users.

TENS therapy requires a device generating a current of a particular frequency, and an electrode, such as a conductive pad, needs to be attached to the human body, for example, the forehead or the back of the head. Due to the limit on the place and time for the TENS therapy, the TENS therapy is not performed in daily life, but only in hospitals, nursing homes, or the like.

DISCLOSURE

Technical Problem

The present invention is directed to provide a bone conduction apparatus that provides music listening or music therapy, and TENS therapy together in daily life.

Technical Solution

The present invention provides a bone conduction apparatus including:

a decoding unit decoding audio data; a digital-to-analog converter converting the decoded audio data to an analog signal, and outputting an analog audio signal; a bone conduction unit converting the analog audio signal to a bone conduction signal, and outputting the bone conduction signal; a metal electrode placed at an outside of a housing in which the bone conduction unit is provided; a frequency generator generating a transcutaneous electrical nerve stimulation (TENS) signal; and a TENS signal amplification unit amplifying the TENS signal, and applying the resulting signal to the metal electrode.

The bone conduction unit may include a first bone conduction unit and a second bone conduction unit, the first bone conduction unit and the second bone conduction unit may be provided in a first housing and a second housing, respectively, and the metal electrode may include a first metal electrode placed at an outside of the first housing, and a second metal electrode placed at an outside of the second housing.

The TENS signal amplification unit may include: a first amplification unit amplifying the TENS signal with the same phase; and a second amplification unit amplifying the TENS signal with the opposite phase, wherein the first amplification unit may apply the TENS signal amplified with the same phase, to the first metal electrode, and the second amplification unit may apply the TENS signal amplified with the opposite phase, to the second metal electrode.

A level of amplification of the TENS signal amplification unit may be variable, and the bone conduction apparatus may further include a user interface through which a user adjusts the level of amplification.

The metal electrode may be a gold-plated copper plate.

A frequency of the TENS signal may be between 70 to 80 Hz.

Advantageous Effects

According to the present invention, the metal electrodes are placed at the outsides of the housings, respectively, in which the respective bone conduction units are provided, and the TENS signals are applied to the metal electrodes, whereby music listening or music therapy, and TENS therapy can be provided together in daily life.

BEST MODE

Figure 1:
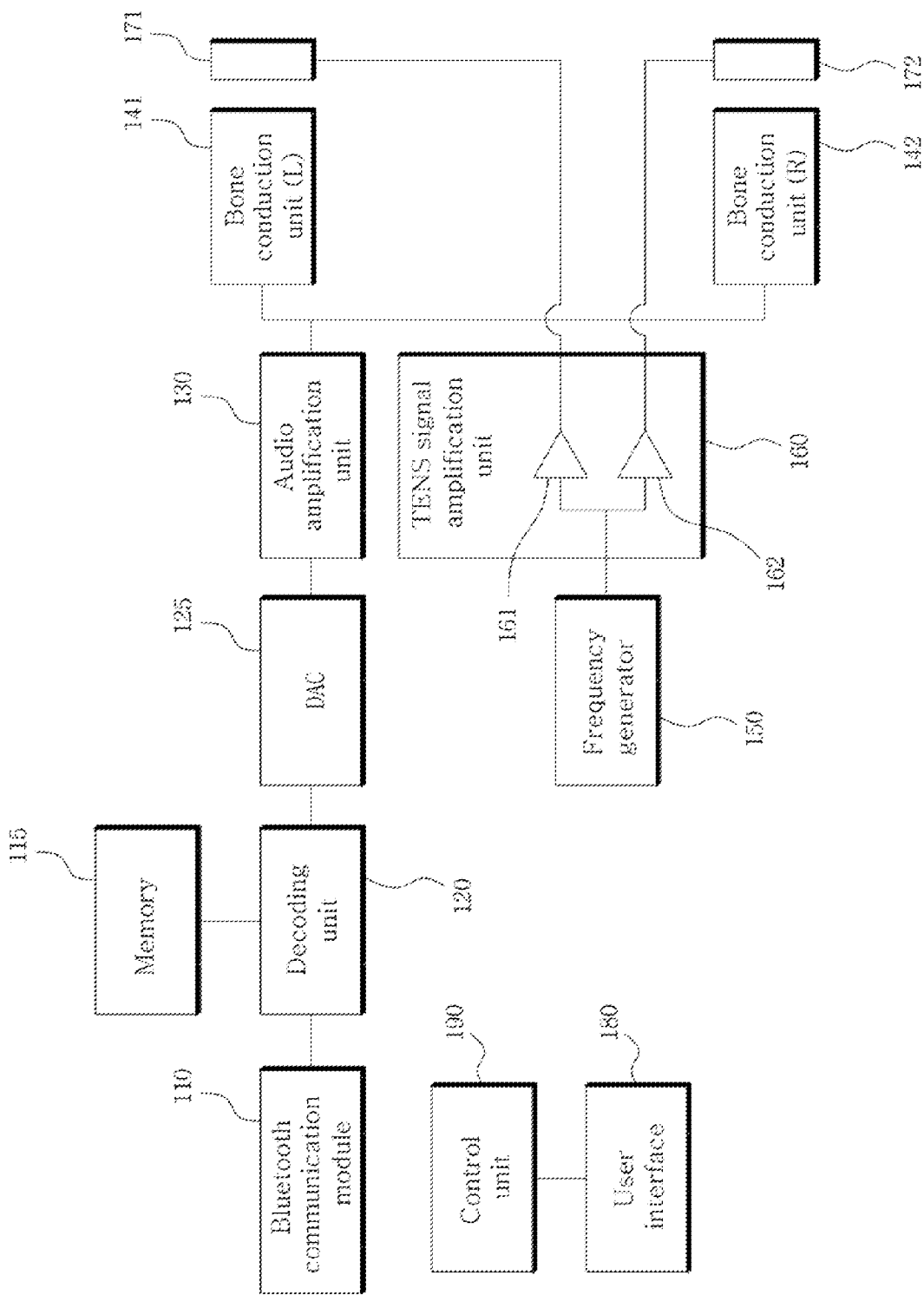
FIG. 1 is a functional block diagram showing a bone conduction apparatus having a TENS therapy function according to an embodiment of the present invention.

Hereinafter, exemplary embodiments of the present invention will be described in detail with reference to the drawings. In the following description and the accompanying drawings, substantially same elements are denoted by the same reference numerals, and a repeated description thereof will be omitted. In addition, in describing the present invention, it is noted that when the detailed description of known functions or configurations related with the present invention may make the gist of the present invention unclear, the detailed description thereof will be omitted.

FIG. 1 is a functional block diagram showing a bone conduction apparatus having a TENS therapy function according to an embodiment of the present invention.

As shown in the figure, the bone conduction apparatus according to the embodiment may include a Bluetooth communication module 110, a memory 115, a decoding unit 120, a digital-to-analog converter 125, an audio amplification unit 130, bone conduction units 141 and 142, a frequency generator 150, a TENS signal amplification unit 160, metal electrodes 171 and 172, a user interface 180, and a control unit 190.

The Bluetooth communication module 110 receives audio data from a music playing device (not shown) by using Bluetooth communication. To this end, the music playing device and the bone conduction apparatus may perform Bluetooth pairing in advance. The music playing device may be, for example, a mp3 player, a CD player, a smartphone, a tablet computer, a TV, or the like that has a Bluetooth communication function.

The memory 115 stores audio data. In the memory 115, basic meditation music or therapy sound data for music therapy may be stored. The user may store desired music in the memory 115. The memory 115 may be built in the bone conduction apparatus. In this case, audio data may be transferred to the memory 115 from other devices, such as a computer, or the like, in a wired or wireless manner. Alternatively, the memory 115 may be a removable memory, for example, an SD card. In this case, audio data may be stored in the memory 115 through other devices, such as a computer, or the like. The memory 115 may be inserted into the bone conduction apparatus.

The Bluetooth communication module 110 or the memory 115 or both may be provided. For example, in the case where only the Bluetooth communication module 110 is provided, audio data is provided through Bluetooth communication. In the case where only the memory 115 is provided, audio data is provided from the memory 115. In the case where both are provided, audio data is provided through Bluetooth communication according to the user's selection, or is provided from the memory 115.

The audio data received through Bluetooth communication or the audio data stored in the memory 115 is generally digital data compressed in a predetermined manner. Therefore, the decoding unit 120 decodes the audio data input through the Bluetooth communication module 110 or the audio data stored in the memory 115, and transmits the resulting data to the digital-to-analog converter 125.

The digital-to-analog converter 125 converts the digital audio data received from the decoding unit 120, to an analog signal, and outputs an analog audio signal.

The audio amplification unit 130 amplifies the analog audio signal to a level suitable for the user to listen (or a level that the user sets), and outputs the resulting signal to the bone conduction units 141 and 142, for example, a left bone conduction unit 141 and a right bone conduction unit 142. The level of amplification of the audio amplification unit 130 may be adjusted according to a user setting through the user interface 180.

The bone conduction units 141 and 142 convert the analog audio signals provided from the audio amplification unit 130, to bone conduction signals, and output the bone conduction signals. Each of the bone conduction units 141 and 142 is usually composed of a frame, a voice coil, a magnet, a diaphragm, and the like.

The frequency generator 150 generates a TENS signal that is a signal of a frequency corresponding to transcutaneous electrical nerve stimulation (TENS). The frequency generator 150 may generate the TENS signal by using a quartz oscillator, or may make a micom generate the corresponding frequency signal so as to generate the TENS signal.

The frequency corresponding to TENS is a frequency used for normal TENS therapy, and may be, for example, a frequency ranging from 1 to 150 Hz. There may be slight differences among people, but in TENS therapy, it is known that the frequency maximally activating endorphins, particularly, beta-endorphins, is about 70 to 80 Hz. Therefore, in order to cause the maximum endorphins, the frequency of the TENS signal may be 70 to 80 Hz (for example, 76 Hz).

The TENS signal generated through the frequency generator 150 is typically a very small signal (for example, several tens mV). Therefore, the TENS signal amplification unit 160 amplifies the TENS signal to a predetermined level (for example, 10 to 30V) that is capable of providing an appropriate stimulation. The level of amplification of the TENS signal amplification unit 160 may be adjusted according to a user setting through the user interface 180.

The TENS signal amplification unit 160 may include a first amplification unit 161 that amplifies the TENS signal from the frequency generator 150 with the same phase; and a second amplification unit 162 that amplifies the TENS signal from the frequency generator 150 with the opposite phase. Thus, the TENS signals in the opposite phases may be output through the first amplification unit 161 and the second amplification unit 162.

That is, the TENS signal of (+) polarity may be output through the first amplification unit 161, and the TENS signal of (−) polarity may be output through the second amplification unit 162. The first amplification unit 161 and the second amplification unit 162 may be variable amplifiers of which the degree of amplification is adjusted according to a user setting, and may be implemented using, for example, a variable resistor, an operational amplifier, and the like. The TENS signal of (+) polarity output through the first amplification unit 161 may be applied to the first metal electrode 171. The TENS signal of (−) polarity output through the second amplification unit 162 may be applied to the second metal electrode 172.

The left bone conduction unit 141 and the right bone conduction unit 142 are provided in a first housing 310 and a second housing 320, respectively, which are manufactured to be in close contact with the user body (for example, the skin surface around the ears). The first metal electrode 171 and the second metal electrode 172 may be placed at the outside of the first housing 310 and the second housing 320, respectively, to be in close contact with the user body (see FIGS. 2 and 3). Alternatively, the first metal electrode 171 may be placed in the second housing 320, and the second metal electrode 172 may be placed in the first housing 310.

The first metal electrode 171 and the second metal electrode 172 may be in the form of a metal plate. The first metal electrode 171 and the second metal electrode 172 are in direct contact with the skin, so the electrodes may be implemented as a gold-plated copper plate to prevent skin problems.

The user interface 180 provides an interface through which the user manipulates the operation of the bone conduction apparatus according to the embodiment of the present invention. For example, the user interface 180 may provide an interface for manipulating an on/off operation of the apparatus, selection of an input source for the audio data (Bluetooth or memory), selection of music, an audio level, an on/off operation of the TENS signal, a TENS signal level, a TENS signal frequency, an audio play timer setting, a TENS signal timer setting, and the like.

According to a preset logic, or the manipulation by the user through the user interface 180, the control unit 190 controls the elements of the apparatus generally, for example, the Bluetooth communication module 110, the decoding unit 120, the digital-to-analog converter 125, the audio amplification unit 130, the frequency generator 150, the TENS signal amplification unit 160, and the like.

According to the embodiment of the present invention, while performing music listening or music therapy with meditation music through the bone conduction units 141 and 142, TENS therapy is performed by applying electrical stimulation of the TENS signals to the skin surface around the ears through the metal electrodes 171 and 172. However, even if it is not only for the purpose of the therapy or pain prevention, the present invention may be used for music listening through the bone conduction units 141 and 142, and simultaneously may be used to cause endorphins to the user in daily life by applying electrical stimulation of the TENS signals.

Mode for Invention

Figure 2:
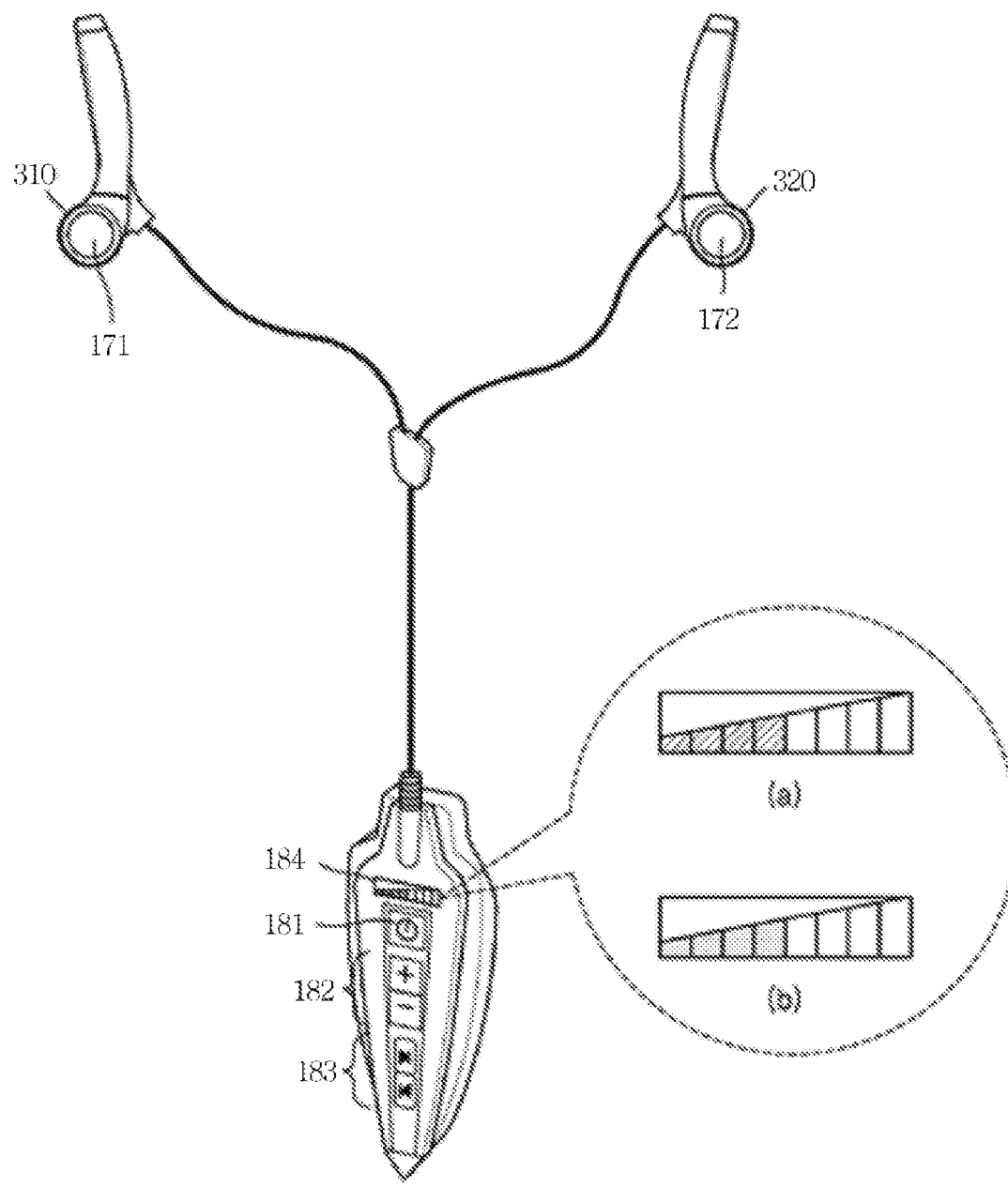
FIG. 2 is a diagram showing an example of a bone conduction apparatus according to an embodiment of the present invention.
Figure 3:
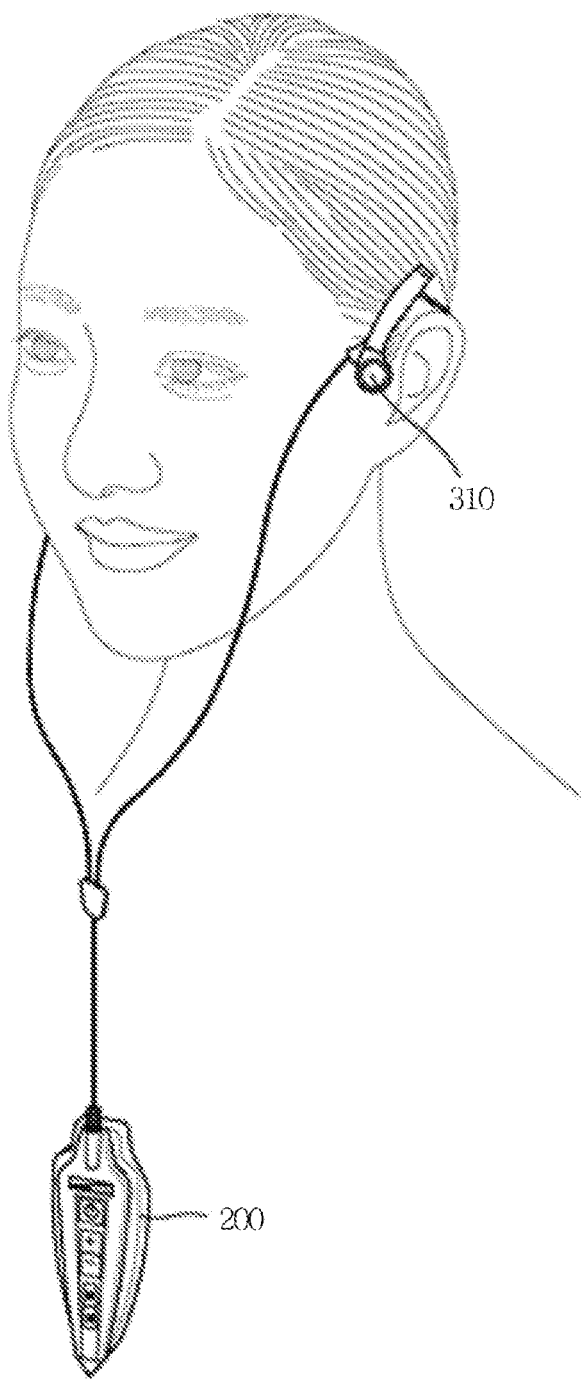
FIG. 3 is a diagram showing an example of the use of a bone conduction apparatus according to an embodiment of the present invention.

FIG. 2 is a diagram showing an example of a bone conduction apparatus according to an embodiment of the present invention. FIG. 3 is a diagram showing an example of the use of a bone conduction apparatus according to an embodiment of the present invention.

Among the elements shown in FIG. 1, the Bluetooth communication module 110, the memory 115, the decoding unit 120, the digital-to-analog converter 125, the audio amplification unit 130, the frequency generator 150, the TENS signal amplification unit 160, the user interface 180, the control unit 190, and the like may be provided in a controller 200. The bone conduction units 141 and 142, and the metal electrodes 171 and 172 may be provided in the respective housings 310 and 320 in the form of earphones. The controller 200 may be connected to the bone conduction units 141 and 142, and the metal electrodes 171 and 172 via a cable. As shown in FIG. 3, the user may carry the controller 200, while wearing the housings 310 and 320 in the form of earphones by using, for example, a tool in the form of a hairband (or in a manner that hangs on the ear without a tool) so that the metal electrodes 171 and 172 are in close contact with the skin surface around the ears.

In addition, referring to FIG. 2, the user interface 180 may include an on-off switch (provided on the side, but not shown), a first button 181, a second button set 182, a third button set 183, an operation state display unit 184, and the like.

The on-off switch sets an on mode and an off mode. Herein, the off mode may be a mode that turns off the TENS function and plays the audio through Bluetooth. The on mode may be a mode that turns on the TENS function and plays the audio stored in the memory 115.

The first button 181 may control the playing and stopping of Bluetooth audio in the off mode. The first button 181 may control the operation of the TENS function and the playing and stopping of the audio stored in the memory 115 in the on mode.

The second button set 182 may adjust the volume of the audio in the off mode. The second button set 182 may set a TENS operation time and may also adjust the volume of the audio in the on mode. For example, in the off mode, a (+) button and a (−) button may increase or decrease the volume. In the on mode, the (+) button and the (−) button may increase or decrease the TENS operation time when pressed shortly, and may increase or decrease the volume when pressed long.

The third button set 183 may control the selection of music, such as the next song or previous song, or the like, in the off mode. The third button set 183 may adjust the intensity of TENS stimulation and may also control the selection of music in the on mode. For example, in the off mode, a (▶) button and a (◀) button may make proceeding to the next song or the previous song. In the on mode, the (▶) button and the (◀) button may increase or decrease the level of the TENS signal when pressed shortly, and may make proceeding to the next song or the previous song when pressed long.

The operation state display unit 184 may display the TENS operation time and the intensity of TENS stimulation. For example, as shown in FIG. 2(a), fundamentally, the operation state display unit 184 displays the remaining TENS operation time in a first color (for example, green) (as described above, when the (+) button and (−) button are pressed shortly in the on mode, the TENS operation time is increased or decreased). In the on mode, when the (▶) button or the (◀) button is pressed shortly, the operation state display unit 184 displays the level of the increased or decreased TENS signal in a second color (for example, red) as shown in FIG. 2(*b*), and after a few seconds, the operation state display unit 184 returns to the state in which the TENS operation time is displayed.

Figure 4:
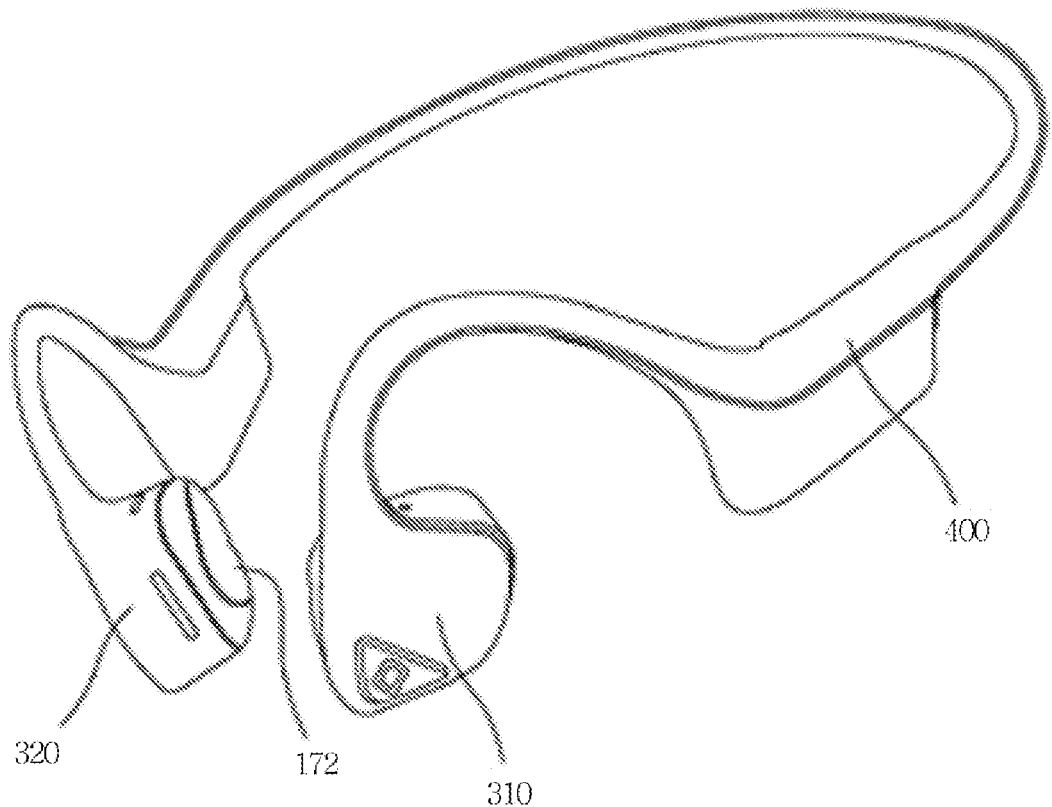
FIG. 4 is a diagram showing another example of a bone conduction apparatus according to an embodiment of the present invention.

FIG. 4 is a diagram showing another example of a bone conduction apparatus according to an embodiment of the present invention. As shown in the figure, the Bluetooth communication module 110, the memory 115, the decoding unit 120, the digital-to-analog converter 125, the audio amplification unit 130, the frequency generator 150, the TENS signal amplification unit 160, the control unit 190, and the like are provided in a tool 400 in the form of a neckband, instead of the controller 200 described above. The bone conduction units 141 and 142, and the metal electrodes 171 and 172 are placed in the respective housings 310 and 320 provided at the opposite ends of the tool 400. Thus, the user may wear the bone conduction apparatus in the form of a neckband. In this case, a smartphone application in conjunction with the bone conduction apparatus through Bluetooth is provided so that all or part of the functions of the user interface 180 may be implemented using the smartphone application.

The exemplary embodiments of the present invention may be described in terms of functional block elements and various processing operations. Such functional blocks may be implemented by any number of hardware and/or software components that execute particular functions. For example, the exemplary embodiments may employ various integrated circuit (IC) components, such as memory elements, processing elements, logic elements, and lookup tables, which may execute various functions under the control of one or more microprocessors or other control devices.

Similarly, where the elements of the present invention are implemented by software programming or software elements, the exemplary embodiments may be implemented by any programming or scripting language such as C, C++, Java, or assembly language, with various algorithms being implemented by any combination of data structures, processes, routines, or other programming elements.

Functional aspects may be implemented by an algorithm that is executed in one or more processors. In addition, the exemplary embodiments may employ the related art for an electronic environment setting, signal processing, and/or data processing. Terms such as "mechanism", "element", "means", and "configuration" may be used in a broad sense, and are not limited to mechanical and physical configurations.

The terms may include the meaning of software routines in conjunction with processors or the like.

Particular implementations described in the exemplary embodiment are exemplary and do not limit the scope of the exemplary embodiment in any way. For the sake of conciseness, descriptions of related electronic configurations, control systems, software, and other functional aspects of the systems may be omitted. In addition, the connection lines or connection members between elements shown in the drawings represent exemplary functional connections and/or physical or logical connections, and may be presented as various alternative or additional functional connections, physical connections, or logical connections in a practical apparatus. In addition, no element may be essential to the practice of the present invention unless the element is specifically described as "essential", "crucial", or so on.

The exemplary embodiments of the present invention have been particularly described. It will be understood by one of ordinary skill in the art that various changes in form and details may be made therein without departing from the spirit and scope of the invention as defined by the following claims. Thus, the exemplary embodiments should be considered in a descriptive sense only and not for purposes of limitation. Therefore, the scope of the invention is defined not by the detailed description of the invention but by the following claims, and all differences within the scope will be construed as being included in the present invention.

INDUSTRIAL APPLICABILITY

The present invention can provide music listening or music therapy, and TENS therapy together in daily life by placing metal electrodes at the outsides of the housings, respectively, in which the respective bone conduction units are provided, and by applying the TENS signals to the metal electrodes.

The invention claimed is:

1. A bone conduction apparatus comprising:
   a receiver configured to receive audio data compressed in a predetermined manner by using wireless communication;
   a digital-to-analog converter configured to convert the audio data to an analog audio signal, and configured to output the analog audio signal;
   a plurality of housings comprising a first housing configured to be contacted with a user body and a second housing configured to be contacted with the user body;
   a plurality of bone conduction units comprising a first bone conduction unit provided in the first housing and a second bone conduction unit provided in the second housing, wherein the plurality of bone conduction unit is configured to convert the analog audio signal to a bone conduction signal and output the bone conduction signal;
   a plurality of metal electrodes comprising a first metal electrode placed at an outside of the first housing and a second metal electrode placed at an outside of the second housing;
   a frequency generator configured to generate a transcutaneous electrical nerve stimulation (TENS) signal; and
   a TENS signal amplification unit connected with the frequency generator and the plurality of metal electrodes, and configured to amplify the TENS signal and apply the amplified TENS signal to the plurality of metal electrodes.

2. The bone conduction apparatus of claim 1, wherein the TENS signal amplification unit comprises:
   a first amplification unit amplifying the TENS signal with the same phase; and
   a second amplification unit amplifying the TENS signal with the opposite phase,
   wherein
      the first amplification unit is configured to apply the TENS signal amplified with the same phase, to the first metal electrode, and
      the second amplification unit is configured to apply the TENS signal amplified with the opposite phase, to the second metal electrode.

3. The bone conduction apparatus of claim 1, further comprising:

a user interface,
wherein
a level of amplification of the TENS signal amplification unit is variable, and
the user interface is configured to adjust the level of amplification.

4. The bone conduction apparatus of claim 1, wherein a frequency of the TENS signal is between 70 Hz to 80 Hz.

\* \* \* \* \*